United States Patent [19]

Aizawa et al.

[11] 3,974,232
[45] Aug. 10, 1976

[54] METHOD FOR PRODUCING CYCLOHEXENE BY DEHYDRATION OF CYCLOHEXANOL

[75] Inventors: Hideyuki Aizawa, Konan; Akio Kuroda, Nagoya; Masahiro Minaga, Chita; Kozi Ohnishi; Seikichi Matsuhisa, both of Nagoya, all of Japan

[73] Assignee: Toray Industries, Inc., Tokyo, Japan

[22] Filed: June 24, 1975

[21] Appl. No.: 590,017

[30] Foreign Application Priority Data
June 29, 1974   Japan.............................. 49-74747

[52] U.S. Cl............................................ 260/666 A
[51] Int. Cl.².......................................... C07C 5/00
[58] Field of Search................................. 260/666 A

[56] References Cited
UNITED STATES PATENTS

| | | | |
|---|---|---|---|
| 2,406,632 | 8/1946 | Pines et al. ..................... | 260/666 A |
| 2,957,034 | 10/1960 | Eschard .......................... | 260/666 A |
| 3,275,698 | 9/1966 | Parish ............................. | 260/666 A |
| 3,342,879 | 9/1967 | Pine ................................ | 260/666 A |
| 3,345,425 | 10/1967 | Rai.................................. | 260/666 A |
| 3,586,720 | 6/1971 | Knepper et al. ................ | 260/666 A |
| 3,652,674 | 3/1972 | Hausen et al................... | 260/666 A |
| 3,780,127 | 12/1973 | Young et al. .................... | 260/666 A |

Primary Examiner—Veronica O'Keefe

[57] ABSTRACT

Cyclohexanol is dehydrated to cyclohexene by heating it in the presence of a heteropolyacid catalyst. The heteropolyacid is selected from tungstophosphoric acid, tungstosilicic acid, molybdophosphoric acid and molybdosilicic acid. Tungstophosphoric acid can be improved in its catalytic performance by calcination. The dehydration reaction is preferably carried out in liquid phase continuously removing cyclohexene by distillation.

13 Claims, No Drawings

METHOD FOR PRODUCING CYCLOHEXENE BY DEHYDRATION OF CYCLOHEXANOL

This invention relates to a method for producing cyclohexene by dehydration of cyclohexanol. More specifically the present invention relates to a method for producing cyclohexene by dehydrating cyclohexanol in the presence of dehydration catalyst selected from tungstophosphoric acid, molybdophosphoric acid, tungstosilicic acid and molybdosilicic acid.

Dehydration of cyclohexanol is a well-known reaction and various kinds of dehydration catalysts have been proposed. For example, sulfuric acid, phosphoric acid, boric acid, alumina and silica-alumina are catalysts generally applicable to dehydration of alcohols. In addition to them, molybdenum sulfide ($MoS_2$) (U.S. Pat. No. 3,342,879), a mixture of about equal amount of polyphosphoric and concentrated sulfuric acids (U.S. Pat. No. 3,345,425), a supported osmium (U.S. Pat.No. 3,121,758), a mixture of polyglycol ether and mineral acid (U.S. Pat. No. 3,275,698), an ion-exchange resin (German Patent No. 887040), acids, whose dissociation constants in water are at least $1 \times 10^{-6}$ and which contain halogen anion, or substances forming such acids (German Patent Publication DOS 2052782) and polybenzimidazol or phthlocyanine (French Patent No. 382070) have been proposed as dehydration catalysts.

Dehydration reaction of cyclohexanol is usually carried out either in a liquid phase using a strong acid catalyst such as sulfuric acid, phosphoric acid and sulfonic acid etc. or in a gas phase at a high temperature using a solid catalyst such as alumina, silica-alumina or phosphate.

A typical example of liquid phase dehydration to produce cyclohexene is described in Organic Synthesis Collective Volume 1, page 183 (1967), wherein concentrated sulfuric acid is used as a catalyst. This method, however, can not be applied to commercial production of cyclohexene because of a large amount of tarry-products and its comparatively low yield, i.e. less than 90%.

In a gas phase dehydration, alumina is the most popular catalyst. In this reaction, however, it is difficult to supress the side reactions such as isomerization and disproportionation of cyclohexene. By-products from such side reactions are methylcyclopentenes, cyclohexane and benzene etc.. They are very difficult to separate out from cyclohexene and cause to deteriorate the purity of cyclohexene obtained.

On producing cyclohexene by dehydration of cyclohexanol side reactions are liable to occur with a formation of high boiling by-products in comparison with dehydration of lower alcohols, and thereby the activity of the catalyst is instantly deteriorated. Accordingly conventional catalysts useful for linear olefin production are not practical for production of cyclohexene.

Thus an object of the invention is to find a catalyst for dehydration of cyclohexanol having a high activity, a long catalytic life and a high selectivity. Another object of the invention is to provide a practical method for industrial production of cyclohexene.

We have now found that a heteropolyacid selected from tungstophosphoric acid, molybdophosphoric acid, tungstosilicic acid and molybdosilicic acid is an excellent catalyst for dehydration of cyclohexanol.

The present invention is a method for production of cyclohexene which comprises heating cyclohexanol in the presence of at least one heteropolyacid selected from the group consisting of tungstophosphoric acid, tungstosilicic acid, molybdophosphoric acid and molybdosilicic acid, and separating cyclohexene from the reaction mixture.

The heteropolyacid may be represented by a general formula,

wherein A is phosphorus or silicon atom, B is tungsten or molybdenum atom, O is oxygen atom, and $m$, $n$, $x$, $y$, and $z$ are integers.

In the present invention a heteropolyacid having a $y/x$ ratio of 1 to 12 may preferably be used as a catalyst.

The heteropolyacid may also be represented by another general formula,

wherein A, B and O is the same as above and $k$, $l$, $m$, $n$ and $z$ are integers. A heteropolyacid having a $m.y/k.x$ ratio of 1 to 12 is preferably used in the present invention.

The examples of these heteropolyacid are described in J. W. Mellor "A comprehensive Treaties on Inorganic and Theoretical Chemistry" Volume XI, page 661 and 862, Longmans, Green & Co. (1931).

These heteropolyacids may be prepared by various conventional methods. A typical method is described in "Inorganic Synthesis" page 129 and 132, edited by H. S. Booth, McGraw Hill (1939).

These heteropolyacids have a similar catalytic performance. As to tungstophosphoric acid, however, calcination is effective for improving its catalytic activity. It may preferably be calcined at a temperature of 200° to 550°C before use.

The reaction may be carried out either in liquid phase or in gas phase. The reaction temperature may be 100° to 180°C, preferably 130°to 160°C in the liquid phase reaction. A higher reaction temperature can be adopted when the reaction is carried out under pressure. In gas phase reaction the reaction temperature may usually be higher than boiling point of cyclohexanol and lower than 400°C, preferably 200°to 350°C. But a lower reaction temperature may also be adopted on feeding cyclohexanol together with an inert gas for dilution, or in a form of an azeotropic mixture.

When the reaction is carried out in liquid phase the concentration of the catalyst may preferably be at least 0.001 wt% on the basis of cyclohexanol. The catalyst may be fed to the reaction zone as a solution in cyclohexanol or other solvents. Since the heteropolyacid has a high solubility in cyclohexanol, it may preferably be fed as a cyclohexanol solution.

In a batchwise method 0.01 to 50 wt% of the catalyst on the basis of cyclohexanol may be charged. In a continuous method the catalyst may be fed as 0.01 to 50 wt% solution in cyclohexanol or other solvents. Cyclohexene may preferably be removed from the reaction mixture by continuous distillation during the reaction period. The remaining reaction mixture may be continuously drawn out from the reactor and the heteropolyacid may be recovered therefrom by treating the mixture with water or by steam distillation.

In some cases cyclohexanol may be continuously added to the reactor containing a fixed amount of a heteropolyacid catalyst at a rate to compensate the cyclohexanol consumed by the dehydration reaction.

Neither cyclohexene nor cyclohexanol causes any serious side reaction, even when they are heated in a liquid phase in the presence of a heteropolyacid at a relatively high temperature. Accordingly a liquid phase reaction is the most preferable embodiments of the present invention.

When the reaction of the present invention is carried out in gas phase, a catalyst supported on a solid carrier may be used. The carrier preferably used is diatomaceous earth, alumina, silica and active carbon. The amount of the heteropolyacid is 1 - 100 wt% on the basis of a carrier.

In the dehydration reaction of the present invention dichclohexylether is formed as an intermediate under some reaction conditions. This intermediate, however, can be converted to cyclohexene and cyclohexanol under reaction conditions of this invention, because the heteropolyacid can also catalyse this reaction under the same reaction condition. Dicyclohexylether may also be recovered from the reaction mixture as a high boiling component and recycled to the dehydration reaction zone. It may also be converted to cyclohexene and cyclohexanol in a separate reaction apparatus using the same catalyst. Such characteristics of the heteropolyacid seem to contribute to a high selectivity of the dehydration reaction of the present invention. According to the method of the present invention cyclohexene can be produced from cyclohexanol in a high yield and selectivity.

Following examples serve to further illustrate the present invention.

The terms "conversion", "selectivity" and "yield" used in the examples are defined as follows if not otherwise stated.

$$\text{conversion (\%)} = \frac{\text{cyclohexanol reacted (mol)}}{\text{cycohexanol fed (mol)}} \times 100$$

$$\text{selectivity (\%)} = \frac{\text{cyclohexene produced (mol)}}{\text{cyclohexanol reacted (mol)}} \times 100$$

$$\text{yield (\%)} = \frac{\text{cyclohexene produced (mol)}}{\text{cyclohexanol fed (mol)}} \times 100$$

EXAMPLE 1

In a round-bottomed flask of 300 ml capacity fitted with packed column distillation unit, were placed 100 g of cyclohexanol and 10 g of tungstophosphoric acid $P_2O_5.24WO_3.nH_2O$. Small amount of nitrogen gas was bubbled through the reaction mixture in order to have an inert atmosphere. The flask was then heated in an oil bath at 160°C.

The overhead product was collected in a glass receiver and separated into organic and aqueous layers.

The organic phase consists substantially of pure cyclohexene and the amount of impurities such as methylcyclopentenes, cyclohexane and benzene was found to be less than 1 wt%.

After about 6 hours, initially charged cyclohexanol was almost consumed and product ceased to distill out.

An additional 100 g of cyclohexanol was charged into the reaction vessel and followed the same operation. The reaction finished in about 5 hours. By repetition of these processes five times successively, ultimately 500 g of cyclohexanol was treated.

The total conversion of cyclohexanol was 95.6 % and cyclohexene yield was 96.2 % based on total cyclohexanol charged.

Residual catalyst had pale brown color and no tarry product was detected to accumulate.

EXAMPLE 2 – 9

In a glass tube, 1.0 g of cyclohexanol was heated at 170°C with 0.2 g of catalyst for 1 hour.

Low boiling products were refluxed in a closed system under nitrogen atmosphere.

The reaction mixture was cooled and then extracted with small amount of ether to separate organic phase from aqueous solution.

The organic phase was analyzed by gas chromatography and cyclohexene yields were calculated based on initially charged cyclohexanol.

The results are shown in a following table.

Table 1

| Examples | catalyst | cyclohexene yield (mole %) |
|---|---|---|
| 2 | $SiO_2.12WO_3.26H_2O$ | 86.1 |
| 3 | $P_2O_5.24MoO_3.nH_2O$ | 80.5 |
| 4 | $SiO_2.12MoO_3.nH_2O$ | 79.8 |
| 5 | $H_2SO_4$ | 75.4 |
| 6 | $P_2O_5$ | 73.1 |
| 7 | $WO_3$ | 2.0 |
| 8 | $MoO_3$ | 3.8 |
| 9 | $SiO_2$ | 0 |

In examples 5 and 6, the product mixtures were dark brown or tarry black in color, but in examples 2, 3 and 4 they were almost colorless and transparent.

EXAMPLE 10

A mixture of 100 g of cyclohexanol and 10 g of tungstophosphoric acid was placed in a 500 ml roundbottomed flask.

The flask was connected to a distillation unit equipped with an Oldershaw type fractionating column of 20 plates attached to an efficient condenser leading to receiver cooled in an ice bath.

The flask was then heated in an oil bath under nitrogen atmosphere. The oil bath temperature was raised gradually. The reaction was observed to start when the temperature reached about 126°C.

The bath temperature was kept constant at 170°C. throughout the further operation, and additional cyclohexanol was continuously supplied to the reacting mixture at the rate of 75 g/hr.

Products were distilled out from the top of the column at the reflux ratio of 3 and collected in the receiver.

Totally 2.00 kg of cyclohexanol was dehydrated and 1.60 kg of crude cyclohexene which contained 99.2 % cyclohexene, 0.3 % cyclohexanol, and 0.5 % of other impurities was obtained.

Throughout the reaction, no reduction in the reaction rate was observed and the reaction mixture in the flask was almost colorless and transparent.

EXAMPLE 11

A mixture of 95.8 wt% cyclohexanol, 3.8 wt% water and 0.4 wt% tungstophosphoric acid was continuously fed at the rate of 1.44 kg/hr to the bottom of a sieve tray distillation column of 100 mm diameter and with 30 plates.

The still was heated by means of Dowtherm heating medium and the temperature was kept constant at 140°C throughout the operation.

The overhead product which contains about 78.1 wt% of cyclohexene, 21.5 wt% of water and 0.4 wt% of other impurities was collected through water cooled condenser in a glass receiver at the rate of 1.35 kg/hr.

The bottom product which has a composition of about 60 wt% cyclohexanol, 6 wt% catalyst and 34 wt% other high boiling impurities was continuously withdrawn from the bottom of the still at the rate of 0.09 kg/hr.

After 156 hrs continuous operation, total conversion of cyclohexanol was 96 %, one pass yield and selectivity of cyclohexene were 93 % and 95 % respectively.

The resulting bottom product was continuously fed to the top of the same distillation column at the rate of 0.5 kg/hr and water was fed to the bottom at the rate of 0.3 kg/hr. The distillate was separated into a water-rich layer and a cyclohexanol-rich layer. The water-rich layer was recycled to the column as reflux and the cyclohexanol-rich layer was withdrawn as an overhead product at the rate of 0.29 kg/hr.

The overhead product contained 85 wt% of cyclohexanol and 82 % of cyclohexanol fed to the distillation column was recovered. The bottom product was withdrawn at the rate of 0.51 kg/hr and was also separated into two liquid layers. The water-rich layer of the bottom product contained 9wt% of tungstophosphoric acid. 90 % of tungstophosphoric acid fed to the distillation column was recovered. This aqueous solution of tungstophosphoric acid was successfully used as the dehydration catalyst of cyclohexanol.

EXAMPLE 12 – 20

Tungstophosphoric acids with different W/P atomic ratio were synthesized by the following procedure.

Definite amounts of sodiumtungstate $Na_2WO_4.2H_2O$ and secondary sodium phosphate $Na_2HPO_4.12H_2O$ were dissolved in 150 ml of distilled water. Concentrated hydrochloric acid (1.5 times of theoretical amount) was slowly added over a period of ten minutes to the resulting solution with vigorous stirring.

Stirring was continued for further 10 minutes.

The water was evaporated under reduced pressure using a rotary evaporator, and tungstophosphoric acid was extracted from the residue with 200 ml of ethanol.

The solvent was removed at reduced pressure to yield a tungstophosphoric acid catalyst.

All the catalysts prepared according to the above described procedure are shown in Table 2.

Table 2

| Examples | $Na_2WO_4.2H_2O$ (g) | $Na_2HPO_4.12H_2O$ (g) | conc. HCl (ml) | Composition of tungstophosphoric acid | W/P ratio |
|---|---|---|---|---|---|
| 12 | 39.58 | 3.58 | 35 | $P_2O_5.24WO_3.nH_2O$ | 12 |
| 13 | " | 4.30 | 35 | $P_2O_5.20WO_3.nH_2O$ | 10 |
| 14 | " | 5.37 | 35 | $P_2O_5.16WO_3.nH_2O$ | 8 |
| 15 | " | 7.16 | 37 | $P_2O_5.12WO_3.nH_2O$ | 6 |
| 16 | " | 10.74 | 40 | $P_2O_5.8WO_3.nH_2O$ | 4 |
| 17 | 19.79 | " | 24 | $P_2O_5.4WO_3.nH_2O$ | 2 |
| 18 | " | 21.48 | 32 | $P_2O_5.2WO_3.nH_2O$ | 1 |
| 19 | 9.90 | " | 24 | $P_2O_5.WO_3.nH_2O$ | 0.5 |
| 20 | 6.60 | 35.8 | 32 | $P_2O_5.2/5WO_3.nH_2O$ | 0.2 |

Activities of these catalysts were checked by the same procedure as described in example 1 except that the amount of catalyst was 5 g.

Activities were indicated by the volumes of cyclohexene produced during 1 hour and 2 hours as shown in a following Table 3.

Table 3

| Examples | W/P ratio | cyclohexene produced (ml) reaction time 1 hr | reaction time 2 hrs |
|---|---|---|---|
| 12 | 12 | 24 | 55 |
| 13 | 10 | 25 | 52 |
| 14 | 28 | 22 | 50 |
| 15 | 6 | 20 | 45 |
| 16 | 4 | 18 | 39 |
| 17 | 2 | 13 | 27 |
| 18 | 1 | 8 | 17 |
| 19 | 0.5 | 2 | 4 |
| 20 | 0.2 | 0 | –0 |

This result shows the excellent catalytic activity of tungstophosphoric acid with W/P atomic ratio from 1 to 12.

We have also proved it by experiments that the simple mixture of 12-tungstophosphoric acid and phosphoric acid (85%) loses its activity almost linearly or more rapidly as the W/P ratio of the mixture decreases.

EXAMPLE 21

Each of the catalyst samples shown in Table 4 except catalyst No. 1, was prepared by the following procedure.

10.0 g of commercially available tungstophosphoric acid ($P_2O_3.24WO_3.nH_2O$) was placed in a 50 ml alumina crucible and heated in an electric furnace for five hours at the calcination temperature indicated in the table.

The catalytic activity of these catalysts was tested in a dehydration of cyclohexanol to cyclohexene according to the procedure described in Example 1.

At the beginning of the reaction, the amount of cyclohexene produced increases almost linearly with reaction time.

Initial reaction rate was calculated from the slope of this linear part and used as a measure of catalytic activity.

The results are shown in Table 4.

Table 4

| Catalyst No. | 1 | 2 | 3 | 4 | 5 | 6 | 7 | 8 |
| --- | --- | --- | --- | --- | --- | --- | --- | --- |
| Calcination temp. (°C) | no calcination | 300 | 400 | 450 | 500 | 550 | 600 | 700 |
| Initial reaction rate ($\frac{\text{ml-cyclohexene}}{\text{hr}}$) | 20 | 39 | 40 | 47 | 63 | 51 | 2 | 2 |

EXAMPLE 22

A mixture of 1.0 g of dicyclohexylether (purity 99.8%), and 0.2 g of 12-tungstophosphoric acid was placed in a glass tube (10 mm$^\phi$ × 150 mm$^1$) fitted with a air cooled condenser (10 mm$^\phi$ × 620 mm$^1$ glass tube).

Nine of these tubes were set in an aluminum block heater and heated at 160°C under nitrogen atmosphere.

The tube was withdrawn one by one from the heater block and cooled to stop the reaction.

The catalyst was then neutralized with sodium hydroxide aqueous solution and the oil layer was analyzed by gaschromatography.

The results are shown in a following table.

Table 5

| Reaction time (min) | Products | | | |
| --- | --- | --- | --- | --- |
| | DCE | HX | NOL | others |
| 2 | 62.6 | 28.9 | 4.1 | 4.4 |
| 4 | 25.7 | 62.4 | 5.5 | 6.4 |
| 6 | 17.9 | 70.1 | 4.7 | 7.3 |
| 8 | 10.1 | 78.8 | 4.7 | 6.4 |
| 10 | 0.3 | 89.0 | 0.8 | 9.9 |
| 22 | 0 | 73.0 | 0 | 27.0 |
| 30 | 0 | 63.6 | 0 | 36.4 |
| 40 | 0 | 49.5 | 0 | 50.5 |
| 50 | 0 | 33.7 | 0 | 66.3 |

DCE: mole % of dicyclohexyl ether remained unreacted.
HX : mole % of dicyclohexyl ether converted to cyclohexene.
NOL: mole % of dicyclohexyl ether converted to cyclohexanol.

EXAMPLE 23 – 34

Using a reactor and a procedure similar to those of the preceding example, various catalysts were tested for their catalytic activities to produce cyclohexene from dicyclohexyl ether.

After 10 minutes of reaction time, products were analyzed and the results are shown in a following table.

Table 6

| Examples | Catalyst | Products | | | |
| --- | --- | --- | --- | --- | --- |
| | | DCE | HX | NOL | others |
| 23 | tungstophosphoric acid | 13.38 | 79.85 | 5.00 | 1.77 |
| 24 | tungstosilicic acid | 22.81 | 73.40 | 4.08 | (−0.29) |
| 25 | molybdophosphoric acid | 2.41 | 92.11 | 4.51 | 0.97 |
| 26 | $H_2SO_4$ (95%) | 27.15 | 65.74 | 0.86 | 6.25 |
| 27 | $H_3PO_4$ (85%) | 91.92 | 3.95 | 0.37 | 3.76 |
| 28 | $AlCl_3$ | 61.57 | 19.74 | 2.87 | 15.82 |
| 29 | $ZnCl_2$ | 86.86 | 8.58 | 1.30 | 3.26 |
| 30 | Zeolite-Y Fe exchanged | 83.72 | 9.70 | 2.84 | 3.74 |
| 31 | $FeSO_4$ | 85.94 | 10.70 | 0.56 | 2.80 |
| 32 | BiBr | 59.14 | 17.18 | 4.18 | 19.50 |
| 33 | CuS | 97.36 | 0 | 0.08 | 2.56 |
| 34 | $MoS_2$ | 98.18 | 0.39 | 0.25 | 1.18 |

DCE, HX, NOL have same meanings as those of Example 22. It is clearly shown that heteropolyacid has an excellent catalytic activity compared with others.

EXAMPLE 35

A catalyst was prepared in the following manner. 10 g of tungstosilicic acid was dissolved in 25 ml water and 20 g of charcoal of about 3 mm$^\phi$ grain was immersed in the solution, and then water was evaporated to get a dry catalyst supported on charcoal grain.

5 g of the catalyst was charged in a glass tube reactor of 25 mm inner diameter equipped with a 300 ml four-necked round-bottomed flask.

The reactor was heated at 300°C from outside by means of electric heater and the flask at 250°C with mantle heater.

Cyclohexanol was fed continuously by means of automatic microfeeder at the rate of 5 g/hr into the flask, in which cyclohexanol was evaporated and carried into the reactor on nitrogen gas stream.

Product was captured through water cooled condenser and dryice-methanol cold trap.

Oil layer was separated from aqueous layer and analyzed by gaschromatography.

Cyclohexanol conversion was 98.5 %, and cyclohexene yield was 96.4 %.

EXAMPLES 36 – 43

The supported tungstophosphoric acid catalysts shown in the Table 7, were prepared by the following procedure.

6 g of tungstophosphoric acid ($P_2O_5$ 24$WO_3$ n$H_2O$) was dissolved in 20 ml of water. The solution was mixed with the 30 g of a carrier powder and 0.6 g of graphite previously suspended in about 30 ml of water.

Water was then evaporated on a steam bath and the dried catalyst powder was formed into cylindrical tablets of 3 mm diameter.

On preparing a catalyst supported on active carbon, previously formed active carbon grains of about 3 mm size were used instead of powder, and the dried catalyst grains were directly used for the reaction without forming into tablets.

Table 7

| catalyst No. | carrier | tungstophosphoric acid supported (wt %) | graphite added (wt %) |
| --- | --- | --- | --- |
| 1 | $\gamma$-$Al_2O_3$ | 20 | 2 |
| 2 | $SiO_2$ | 20 | 2 |
| 3 | diatomaceous earth | 20 | 2 |
| 4 | active carbon | 20 | 0 |

The catalysts were charged into a glass tube reactor of 18 mm diameter and 500 mm length and heated from outside by means of an electric heater.

When the temperature reached and settled at the reaction temperature, cyclohexanol was fed from the top of the reactor by means of a micro feeder at the constant rate.

The product was collected through water cooled condenser in a glass receiver cooled in an ice bath and fitted with a dry-ice-methanol cold trap at the outlet.

The oil layer was separated from the aqueous layer and analyzed by gaschromatography.

The results are shown in the following table.

Table 8

| Example No. | catalyst No. | catalyst weight (g) | NOL feed rate (g/hr) | NOL conversion (%) | HX selectivity (%) |
|---|---|---|---|---|---|
| 36 | 1 | 17.0 | 4.9 | 100 | 94.5 |
| 37 | 2 | 10.3 | 4.9 | 100 | 93.2 |
| 38 | 3 | 11.7 | 4.9 | 100 | 83.8 |
| 39 | 4 | 8.3 | 4.9 | 100 | 89.9 |

NOL : cyclohexanol  Reaction temperature 200 C
HX : cyclohexene

The intrinsic activities of carrier substances were also checked by the same procedure, and the following results were obtained.

Table 9

| Example No. | catalyst | catalyst weight (g) | NOL feed rate (g/hr) | NOL conversion (%) | HX selectivity (%) |
|---|---|---|---|---|---|
| 40 | $\gamma$-$Al_2O_3$ | 15.0 | 4.9 | 35.6 | 73.4 |
| 41 | $SiO_2$ | 9.5 | 4.9 | 82.6 | 93.4 |
| 42 | diatomaceous earth | 11.0 | 4.9 | 65.3 | 81.0 |
| 43 | active carbon | 8.5 | 4.9 | 12.1 | 28.0 |

What we claim is:

1. A method for producing cyclohexene which comprises heating cyclohexanol in the presence of at least one heteropolyacid selected from the group consisting of tungstophosphoric acid, tungstosilicic acid, molybdophosphoric acid and molibdosilicic acid, and separating cyclohexene from the reaction mixture.

2. A method of claim 1 wherein the heteropolyacid is tungstophosphoric acid.

3. A method of claim 2 wherein the tungstophosphoric acid has a W/P atomic ratio of from 1 to 12.

4. A method of claim 2 wherein the tungsticophosphoric acid is calcined at 200° to 550°C. before use.

5. A method of claim 1 wherein the heteropolyacid is tungstosilicic acid.

6. A method of claim 5 wherein the tungstosilicic acid has a W/Si atomic ratio of from 1 to 12.

7. A method of claim 1 wherein the heteropolyacid is molybdophosphoric acid.

8. A method of claim 7 wherein the molybdophosphoric acid has a Mo/P atomic ratio of from 1 to 12.

9. A method of claim 1 wherein the heteropolyacid is molybdosilicic acid.

10. A method of claim 9 wherein the molybdosilicic acid has a Mo/Si atomic ratio of from 1 to 12.

11. A method of claim 1 wherein the heating is carried out in liquid phase at 100° to 180°C.

12. A method of claim 11 wherein the cyclohexene is continuously removed from the reaction mixture by distillation.

13. A method of claim 12 wherein the remaining reaction mixture is subjected to steam distillation and thereby cyclohexanol and aqueous solution of heteropolyacid catalyst are recovered.

* * * * *